(12) United States Patent
Simmons et al.

(10) Patent No.: US 9,265,470 B2
(45) Date of Patent: Feb. 23, 2016

(54) PIVOTING X-RAY IMAGING DEVICES

(75) Inventors: John Matthew Simmons, Bountiful, UT (US); David E. Barker, Salt Lake City, UT (US); Jan D. Bruening, Salt Lake City, UT (US); Samuel L. Alder, Stansbury Park, UT (US)

(73) Assignee: General Electric Company, Schenectady, NY (US)

( * ) Notice: Subject to any disclaimer, the term of this patent is extended or adjusted under 35 U.S.C. 154(b) by 699 days.

(21) Appl. No.: 13/114,244

(22) Filed: May 24, 2011

(65) Prior Publication Data
US 2012/0300909 A1 Nov. 29, 2012

(51) Int. Cl.
*A61B 6/00* (2006.01)

(52) U.S. Cl.
CPC .............. *A61B 6/4441* (2013.01); *A61B 6/447* (2013.01); *A61B 6/4405* (2013.01); *A61B 6/548* (2013.01)

(58) Field of Classification Search
CPC .............................. A61B 6/4441; A61B 6/4447
USPC ........................................ 378/196, 197, 198
See application file for complete search history.

(56) References Cited

U.S. PATENT DOCUMENTS

| 751,663 | A |   | 2/1904 | Livingstone | |
|---|---|---|---|---|---|
| 2,926,256 | A |   | 2/1960 | Rankin | |
| 3,456,114 | A | * | 7/1969 | Gray | 378/197 |
| 3,824,397 | A | * | 7/1974 | Bauer et al. | 378/195 |
| D291,916 | S |   | 9/1987 | Davis | |
| 4,716,581 | A | * | 12/1987 | Barud | 378/198 |
| 4,763,345 | A |   | 8/1988 | Barbaric et al. | |
| 4,856,036 | A | * | 8/1989 | Malcolm et al. | 378/116 |
| 5,074,501 | A |   | 12/1991 | Holttae | |
| D391,148 | S |   | 2/1998 | Rosen | |
| D391,945 | S |   | 3/1998 | Rosen | |
| 5,743,499 | A |   | 4/1998 | Wang | |
| 5,980,107 | A | * | 11/1999 | Kusch | 378/194 |
| 6,425,303 | B1 |   | 7/2002 | Brogaardh et al. | |
| 8,152,192 | B2 |   | 4/2012 | Dougherty | |
| 2008/0013690 | A1 |   | 1/2008 | Lurz et al. | |
| 2008/0013692 | A1 | * | 1/2008 | Maschke | 378/198 |
| 2010/0195790 | A1 |   | 8/2010 | Machado et al. | |

OTHER PUBLICATIONS

Unofficial English translation of Chinese Office Action issued in connection with corresponding CN Application No. 201210179127.5 on Jun. 10, 2015.

* cited by examiner

*Primary Examiner* — Glen Kao (57) ABSTRACT

Systems and methods for rotating X-ray devices are disclosed. The systems and methods use X-ray devices with an X-ray imaging arm orbitally rotating about pivot joints that are physically attached to the X-ray imaging arm. The pivot joint coincides with the center of gravity for the X-ray imaging arm. The X-ray device has an X-ray imaging arm with an X-ray source and detector respectively disposed at nearly opposing locations of the imaging arm. The pivot joint can serve as an axis of orbital rotation around which the imaging arm pivots. The pivot joint can be pivotally attached to a first end of an X-ray imaging arm fork, which has a second end attached to an X-ray imaging arm support structure. The imaging arm fork can include a lateral pivot joint that provides a lateral axis of rotation for the imaging arm. The fork can contain one or two arms.

21 Claims, 10 Drawing Sheets

PIVOTING X-RAY IMAGING DEVICES

FIELD

This application relates generally to X-ray equipment. More specifically, this application relates to systems and methods for rotating or pivoting an X-ray imaging arm, such as a C-arm, about a pivot joint that is physically attached to or part of the imaging arm.

BACKGROUND

A typical X-ray imaging system comprises an X-ray source and an X-ray detector. X-rays emitted from the X-ray source can impinge on the X-ray detector and provide an X-ray image of the object or objects that are placed between the X-ray source and the detector. In one type of X-ray imaging system, a fluoroscopic imaging system, the X-ray detector is often an image intensifier or, more recently, a flat panel digital detector.

In addition to the X-ray source and the X-ray detector, the typical fluoroscopic imaging system can comprise a main assembly, a movable support assembly, and a gantry or imaging arm assembly. The main assembly is coupled to the movable support assembly, and the support assembly supports the movable gantry or imaging arm assembly. In mobile imaging systems, the main assembly typically includes wheels for moving and/or positioning the imaging system.

Fluoroscopic imaging systems can be either fixed or mobile. For instance, fixed fluoroscopic imaging systems often include a gantry that is secured to a floor, wall, or ceiling. Additionally, mobile fluoroscopic imaging systems are movable so that they can be used in a variety of clinical environments, such as radiology and surgery departments of a medical facility. The mobile fluoroscopic imaging systems may include a C-arm, O-arm, L-arm, or another imaging arm assembly.

In some configurations, a C-arm assembly of a fluoroscopic imaging system remains stationary relative to a subject for single angle imaging. In other configurations, however, the C-arm assembly moves relative to the subject in order to acquire images from multiple angles. In some arrangements the C-arm assembly is manually repositioned to generate images from different angles while in other arrangements the C-arm assembly is moved along a predetermined path by operation of a motorized drive mechanism in order to generate images from multiple angles.

SUMMARY

This application relates generally to X-ray devices. In particular, this application relates to systems and methods for providing an X-ray device in which an X-ray imaging arm (such as a C-arm) can pivotally rotate in an orbital manner about a pivot joint that is physically attached to the X-ray imaging arm. The X-ray device can have an X-ray imaging arm that has an X-ray source and an X-ray detector which are respectively disposed at nearly opposing locations of the imaging arm. The pivot joint can serve as an axis of orbital rotation around which the imaging arm pivots in an orbital fashion. The pivot joint can be pivotally attached to a first end of an X-ray imaging arm fork, which, in turn, can have its second end attached to an X-ray imaging arm support structure (such as a mobile cart). The imaging arm fork can further include a lateral pivot joint that provides a lateral axis of rotation for the imaging arm.

BRIEF DESCRIPTION OF THE DRAWINGS

The following description can be better understood in light of the Figures, in which.

The Figures illustrate specific aspects of the described X-ray imaging devices and methods for making and using such devices. Together with the following description, the Figures demonstrate and explain the principles of the structures, methods, and principles described herein. In the drawings, the thickness and size of components may be exaggerated or otherwise modified for clarity. The same reference numerals in different drawings represent the same element, and thus their descriptions will not be repeated. Furthermore, well-known structures, materials, or operations are not shown or described in detail to avoid obscuring aspects of the described devices.

DETAILED DESCRIPTION

The following description supplies specific details in order to provide a thorough understanding. Nevertheless, the skilled artisan will understand that the described X-ray imaging devices and associated methods of making and using such X-ray imaging devices can be implemented and used without employing these specific details. Indeed, the described X-ray imaging devices and associated methods can be placed into practice by modifying the described systems and methods and can be used in conjunction with any other apparatus and techniques conventionally used in the industry. For example, while the description below focuses on methods for making and using orbitally-pivoting X-ray imaging devices that comprise an X-ray imaging arm, such as a mini C-arm, the described X-ray imaging devices can comprise virtually any other suitable type of X-ray equipment in which an X-ray imaging arm can pivot in an orbital fashion around a pivot joint that is attached to the imaging arm. Some suitable examples of such X-ray imaging arms can include a standard C-arm, a compact style C-arm, a mini C-arm, and a non-circular arm.

This application relates to systems and methods for orbitally rotating or pivoting an X-ray imaging arm, such as a C-arm, about a pivot joint that is physically attached to the imaging arm. Indeed, unlike some conventional C-arm positioning apparatus 10 (shown in FIG. 1 on the right) in which a conventional C-arm X-ray device 15 is configured to rotate around a virtual pivot point 20 (or an axis of orbital rotation 25 that is disposed in a gap 30 (e.g., in the air) between an X-ray source 35 and an X-ray detector 40), the described orbitally-pivoting X-ray imaging devices 100 are each configured to have an X-ray imaging arm 105 that can pivot orbitally about an orbital pivot joint 110 that is physically connected to—or part of—an X-ray imaging arm 105.

Figure 1:
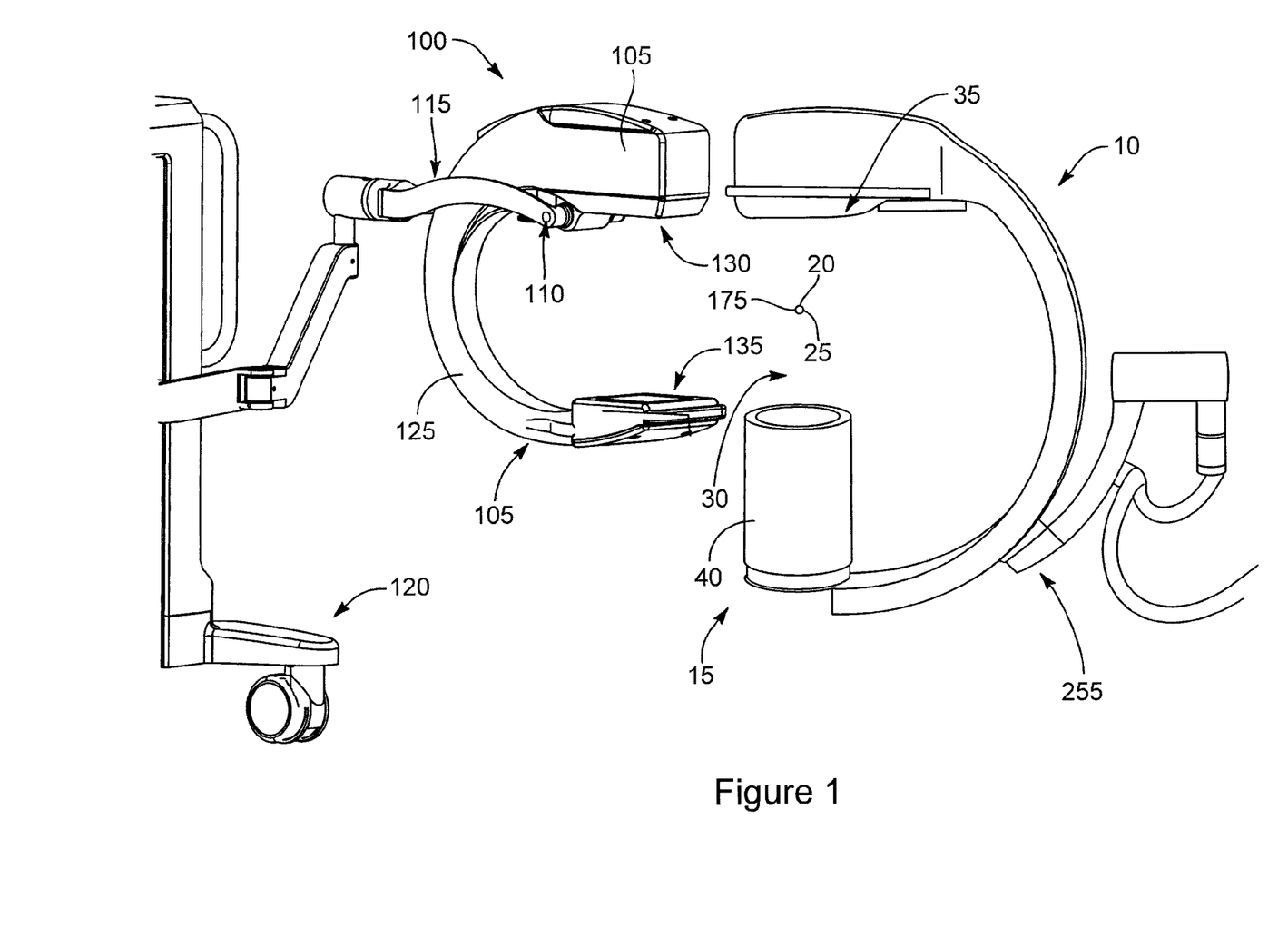
FIG. 1 shows a side view of some embodiments of an orbitally-pivoting X-ray imaging device and some embodiments of a conventional C-arm X-ray positioning apparatus.

FIG. 1 shows some embodiments in which the orbitally-pivoting X-ray imaging device 100 (or pivoting X-ray device) comprises the X-ray imaging arm 105 (or imaging arm), an X-ray imaging arm fork 115 (or imaging arm fork), and an X-ray imaging arm support structure 120 (or support structure). The pivoting X-ray device 100 can comprise any suitable imaging arm 105 that allows the pivoting X-ray device to be used to take X-ray images of a portion of a patient's body (not shown). For example, the imaging arm can comprise a mini C-arm, a standard C-arm, an O-arm, and L-arm, a compact style C-arm, and/or a non-circular arm. By way of illustration, FIG. 1 shows some embodiments in which the imaging arm 105 comprises a mini C-arm 125.

The imaging arm 105 can also comprise any suitable component that allows it to be used to take X-ray images of a portion of a patient's body. For example, FIG. 1 shows some embodiments in which the imaging arm 105 comprises an X-ray source 130, an X-ray detector 135, and the orbital pivot joint 110.

The imaging arm 105 can comprise any suitable X-ray source 130 and X-ray imaging detector 135 that allow the pivoting X-ray device 100 to take X-ray images. In this regard, the X-ray source can comprise any source that generates and emits X-rays, including a standard X-ray source, a rotating anode X-ray source, a stationary or fixed anode X-ray source, a solid state X-ray emission source, and/or a fluoroscopic X-ray source. Moreover, the X-ray detector can comprise any detector that detects x-rays, including an image intensifier and/or a digital flat panel detector.

Figure 2:
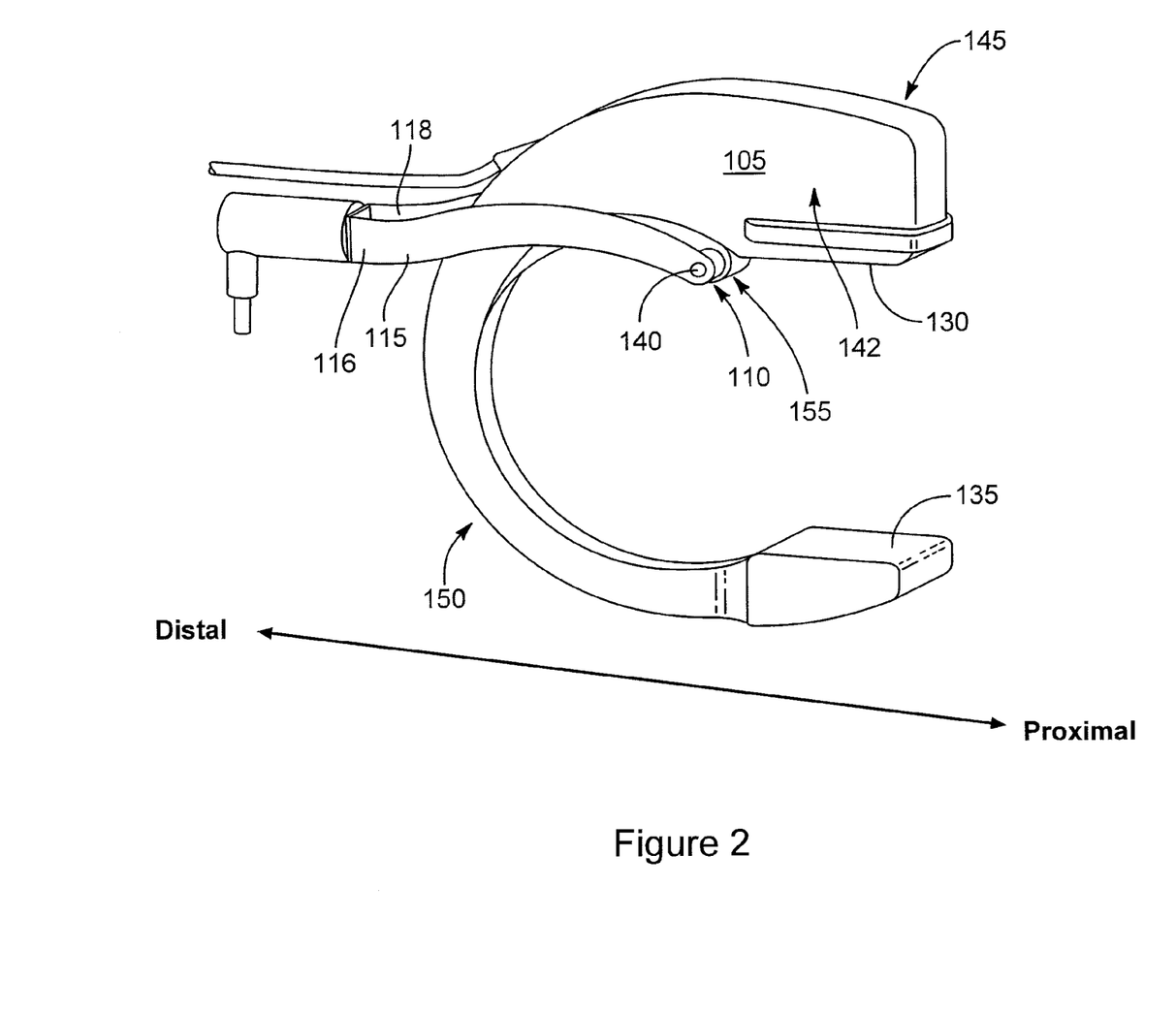
FIG. 2 shows a side perspective view of some embodiments of an X-ray imaging arm.

The pivot joint (or orbital pivot joint) 110 can comprise any suitable pivot joint that can be attached to the imaging arm 105 and that can allow the imaging arm to rotate orbitally around it. FIG. 2 shows some embodiments in which the orbital pivot joint 110 includes a pivot pin 140, which is attached to the imaging arm fork 115 and extends through the imaging arm 105 in a manner that allows the imaging arm to rotate orbitally around the pin.

In another example of a suitable orbital pivot joint 110, a first member (e.g., a shaft) extends at a first lateral side (e.g., side 142) and a second member extends from a second lateral side (e.g., second lateral side 145) of the imaging arm 105. In this example, the first and the second member are, respectively, received by a receptacle in a first arm (e.g., first support arm 116) and second arm (e.g., second support arm 118) of the imaging arm fork in a manner that allows the imaging arm to pivot orbitally around these members.

In still another example of a suitable orbital pivot joint 110, a first member and/or a second member extend medially from a first arm (e.g., first support arm 116) and/or a second arm (e.g., second support arm 118) of the imaging arm fork 115 and respectively extend into a first and/or second recess on a first (e.g., side 142) and/or second (e.g., side 145) lateral side of the imaging arm 105 in a manner that allows the imaging arm to orbitally rotate around one or both of the members.

In yet another example of a suitable orbital pivot joint 110, the orbital pivot joint can comprise one or more bushings, bearings, bearing raceways, washers, conical sliding or rubbing surfaces, and/or any other suitable component that allows the imaging arm 105 to pivot about the pivot joint in an orbital manner.

Figure 3:
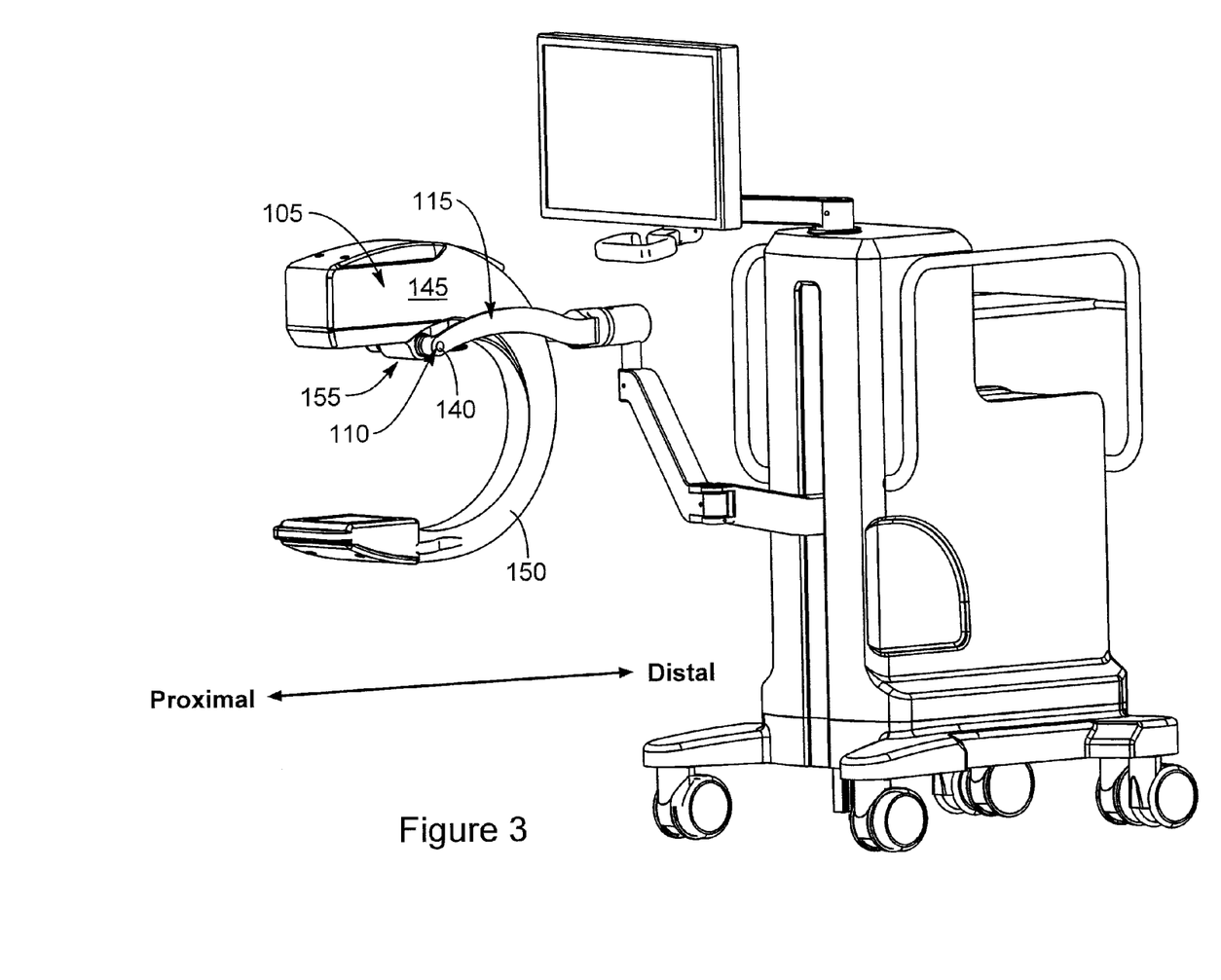
FIG. 3 shows a side view of some embodiments of the X-ray imaging arm.

The orbital pivot joint 110 can be disposed in any suitable location on the imaging arm 105 that allows the imaging arm to rotate as described herein. By way of example, the orbital pivot joint can be disposed adjacent to (e.g., proximal to, above, below, and/or at) the X-ray source 130, adjacent to (e.g., proximal to, above, below, and/or at) the X-ray detector 135, or on an elongated portion of the imaging arm 105 (e.g., elongate portion 150) that extends between the X-ray source 130 and the X-ray detector 135. By way of illustration, FIGS. 2 and 3 show some embodiments in which the orbital pivot joint 110 is disposed relatively near to the X-ray source 130, i.e., at a protuberance 155 that extends below the X-ray source and towards the X-ray detector 135.

The orbital pivot joint 110 can provide the imaging arm 105 with any degree of orbital rotation that allows the imaging arm to be used to take X-ray images. In some embodiments, the orbital pivot joint allows the imaging arm to orbitally rotate more than about 135 degrees. In other embodiments, the orbital pivot joint allows the imaging arm to rotate more than about 180 degrees. In still other embodiments, the orbital pivot joint allows the imaging arm to rotate more than about 200 degrees. In yet other embodiments, the orbital pivot joint allows the imaging arm to rotate more than about 220 degrees. In even other embodiments, the orbital pivot joint allows the imaging arm to orbitally rotate about 360 degrees. In still other embodiments, this pivot allows rotation of at least 135 degrees in one direction and a total of at least 270 degrees in both directions. In other embodiments, the orbital pivot joint allows the imaging arm to rotate in any combination or sub-range of these degrees.

Figure 4:
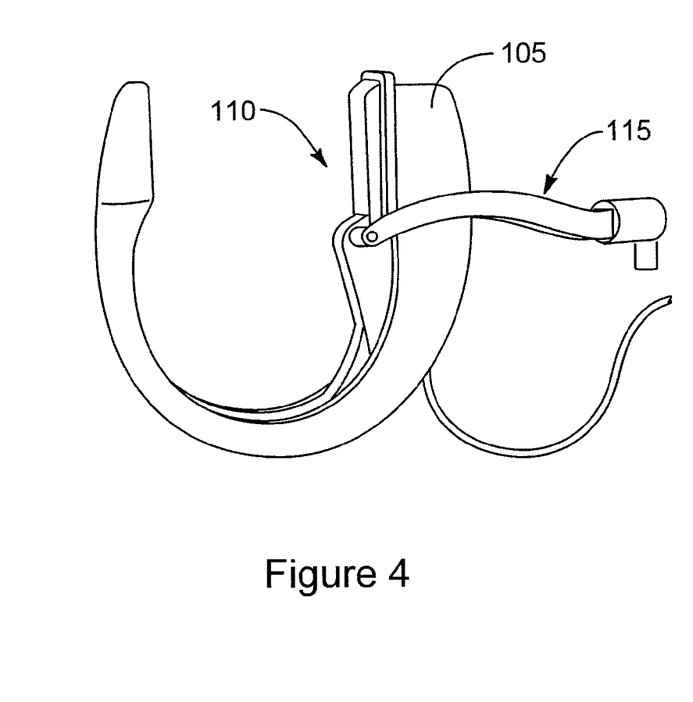
FIG. 4 shows a side view of some embodiments of the X-ray imaging arm, rotated to a under scan position.

The orbital pivot joint 110 can allow the imaging arm 105 to under scan (as shown in FIG. 4) by any suitable amount that still allows the imaging arm to be used to take X-ray images. In some configurations, the term under scan may refer to a counter clockwise orbital rotation of the imaging arm from its standard position (shown in the left view of FIG. 1), or a position in which the X-ray beam runs substantially perpendicular to a horizontally level floor. Indeed, in some embodiments, the orbital pivot joint allows the imaging arm to under scan by an amount that is greater than a rotational amount selected from about 90 degrees, about 120 degrees, about 140 degrees, and about 150 degrees. In other embodiments, this under scan amount can be any combination or sub-range of these degrees.

Figure 5:
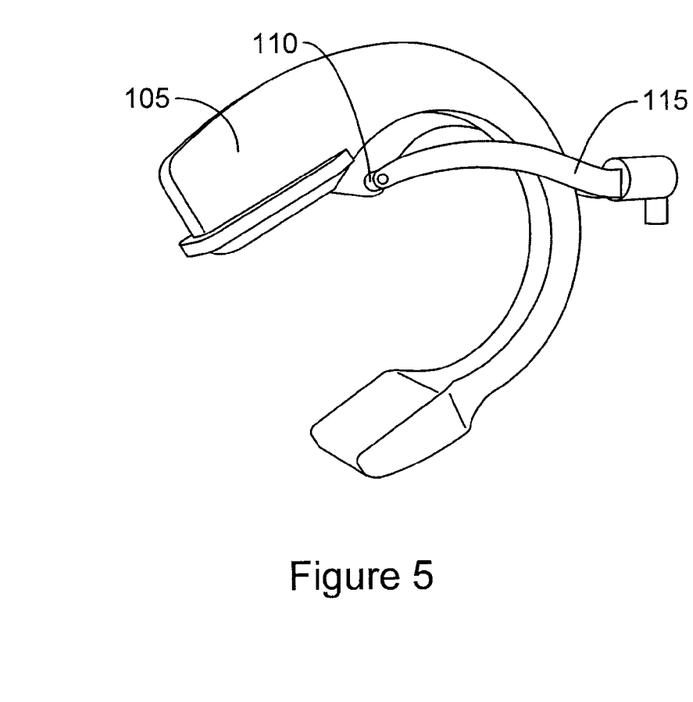
FIG. 5 shows a side view of some embodiments of the X-ray imaging arm, rotated to a over scan position.

The orbital pivot joint 110 can also allow the imaging arm 105 to over scan (as shown in FIG. 5) by any suitable amount that allows the imaging arm to take X-ray images. In some configurations, the term over scan may refer to a clockwise orbital rotation of the imaging arm from its standard position (shown in the left view of FIG. 1). Indeed, in some embodiments, the orbital pivot joint allows the imaging arm to over scan by an amount that is greater than a rotational amount selected from about 30 degrees, about 45 degrees, about 60 degrees, about 80 degrees, about 90 degrees, and about 120 degrees. In other embodiments, this over scan amount can be any combination or sub-range of these degrees.

Figures 6, 7:
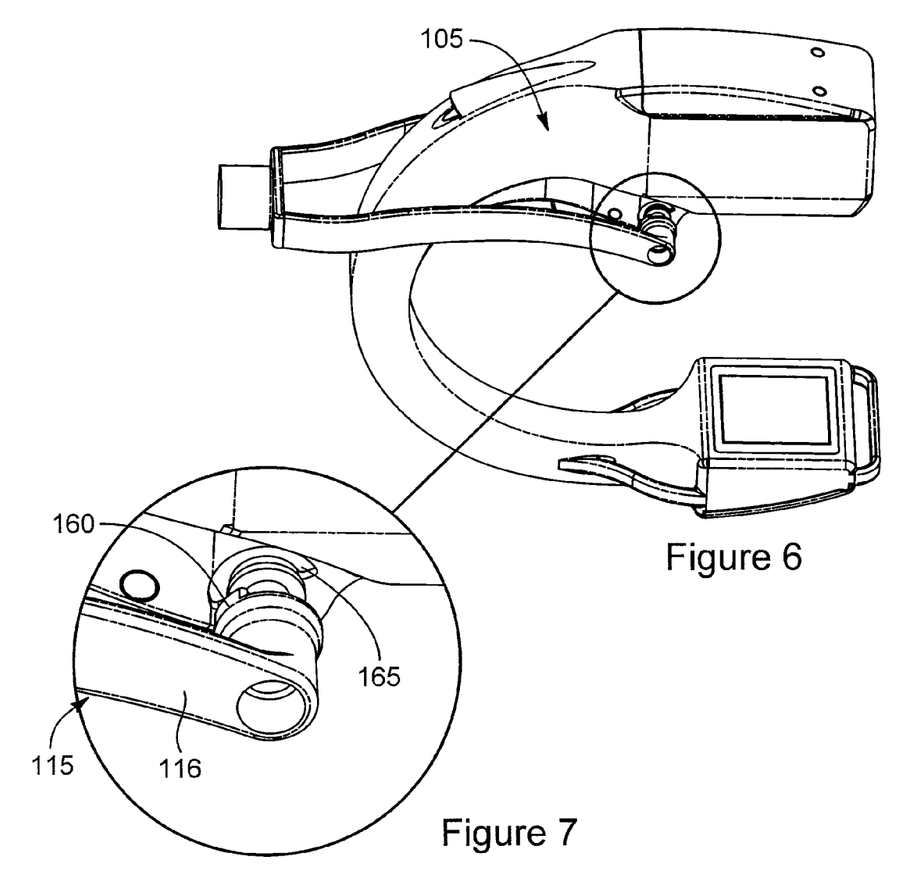
FIG. 6 shows a perspective view of some embodiments of the X-ray imaging arm.
FIG. 7 shows a detailed view of a portion of the X-ray imaging arm from FIG. 6.

The orbital pivot joint 110 can be configured to allow the imaging arm 105 to have any suitable degree of orbital rotation. In some embodiments, the pivoting X-ray device 100 comprises one or more stop mechanisms that limit the image arm's range of orbital rotation. In this manner, the stop mechanism can prevent a power cable connected to the imaging arm from being twisted or becoming wrapped around the orbital pivot joint. Indeed, in one example, the stop mechanism comprises a tab that extends from the imaging arm can be configured to move the length of a corresponding groove formed in the imaging arm fork. In another example, FIGS. 6 and 7 show some embodiments in which the stop mechanism comprises a tab 160 extending medially from one of the imaging arm fork's arms (e.g., first support arm 116) is configured to only slide along the length of a corresponding groove 165 in the imaging arm 105.

Figure 8:
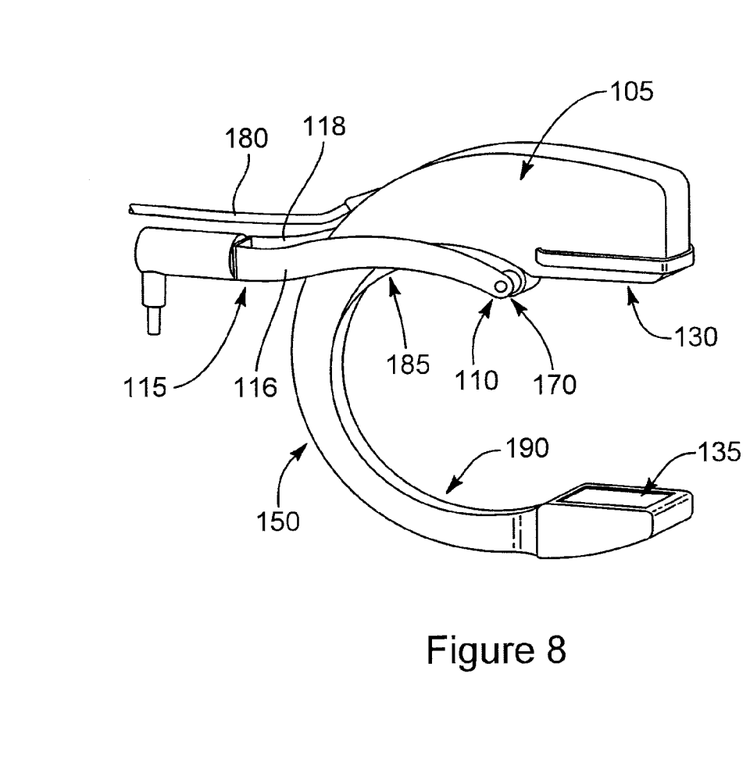
FIG. 8 shows a side perspective view of some embodiments of the X-ray imaging arm.

The imaging arm 105 can be configured to support the X-ray source 130 and the X-ray detector 135 so that they are respectively disposed at nearly opposite ends of the imaging arm, substantially face each other, and/or can rotate around the orbital pivot joint 110. For instance, the imaging arm can have any suitable shape. By way of example of such shapes, the imaging arm can be substantially convex, C-shaped, V-shaped, U-shaped, polygonal, square shaped, parabolically shaped, circular, non-circular, ellipsoidal, irregularly shaped, etc. By way of illustration, FIG. 8 shows some embodiments in which the imaging arm 105, from its side view, has a substantially C-shaped appearance.

The imaging arm 105 can have its weight distributed so that its center of gravity can be disposed in any location that allows the arm to orbitally rotate about the orbital pivot joint 110. For instance, the imaging arm's center of gravity can be disposed adjacent to the X-ray source 130, adjacent to the X-ray detector 135, on the elongate portion 150 of the imaging arm, and/or anywhere on the arm geometry. By way of illustration, FIG. 8 shows some embodiments in which the image arm's center of gravity 170 is disposed adjacent to the X-ray source 130.

In some embodiments, the imaging arm (unlike some conventional C-arm X-ray devices 15 shown in FIG. 1 that have a center of gravity 175 substantially coinciding with the C-arm's virtual pivot point 20) has its weight dispersed so that its center of gravity 170 substantially coincides or overlaps with its axis of orbital rotation (e.g., the orbital pivot joint 110). In such embodiments, the imaging arm can tend to remain at specific location in its orbital rotation without being substantially repositioned or rotated by the force of gravity. In this regard, the imaging arm can be configured so that its center of gravity substantially coincides with the axis of orbital rotation (e.g., the orbital pivot joint) when a power and/or data cable 180 (as shown in FIG. 8) is attached directly to the imaging arm 105 and/or through some other method (e.g., via the orbital pivot joint).

Figure 9:
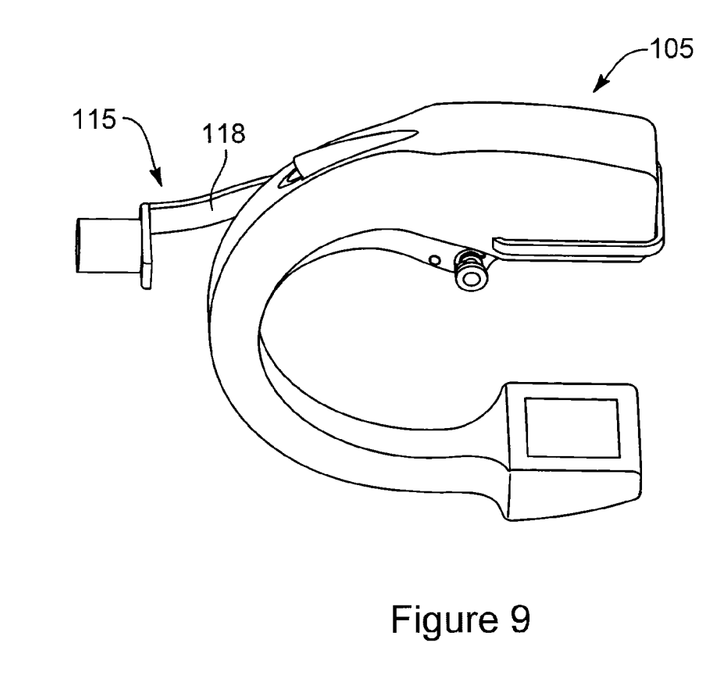
FIG. 9 shows a side view of some embodiments of a X-ray imaging arm support fork comprising a single support arm.

As to the imaging arm fork 115, it can be configured to support the imaging arm 105, attach the imaging arm to the support structure 120, provide the imaging arm with an axis of lateral rotation, provide the imaging arm with an axis of horizontal rotation, and/or provide the imaging arm with an axis of rotation perpendicular to the orbital rotation axis. Thus, the imaging arm fork can comprise any suitable component or characteristic that allows it to function in this manner. In one example, the imaging arm fork 115 can comprise any suitable number of imaging arm support arms, including 1, 2, or more. By way of illustration, FIG. 8 shows some embodiments in which the imaging arm fork 115 comprises 2 support arms 116 and 118. FIG. 9 shows other embodiments in which the imaging arm fork 115 comprises a single support arm 118.

The imaging arm fork's support arms (e.g., support arms 116 and 118) can be any suitable length and be any suitable distance apart. In some embodiments, the support arms are long enough and are spaced far enough apart to allow the imaging arm 105 to rotate about 360 degrees. In other embodiments, the support arms are spaced close enough together to prevent the X-ray source 130 and/or X-ray detector 135 from passing therethrough. Similarly, in other embodiments, the support arms are short enough that a portion of the imaging arm (e.g., the elongated portion 150) is configured to contact the imaging arm fork when the imaging arm is rotated a certain amount. Thus, the imaging arm fork can be configured to limit the imaging arm's orbital rotation.

The support arms of the imaging arm fork 115 (e.g., support arms 116 and 118) can be any suitable shape. For instance, the support arms can be substantially straight, curved, angled, irregular, and any combination thereof. By way of illustration, FIG. 8 shows some embodiments in which the first 116 and second 118 support arms comprise a substantially curved portion 185, which may allow the imaging arm 105 to be moved to an over scan position without substantially blocking the space defined by the inner perimeter 190 of the imaging arm 105.

Figure 10:
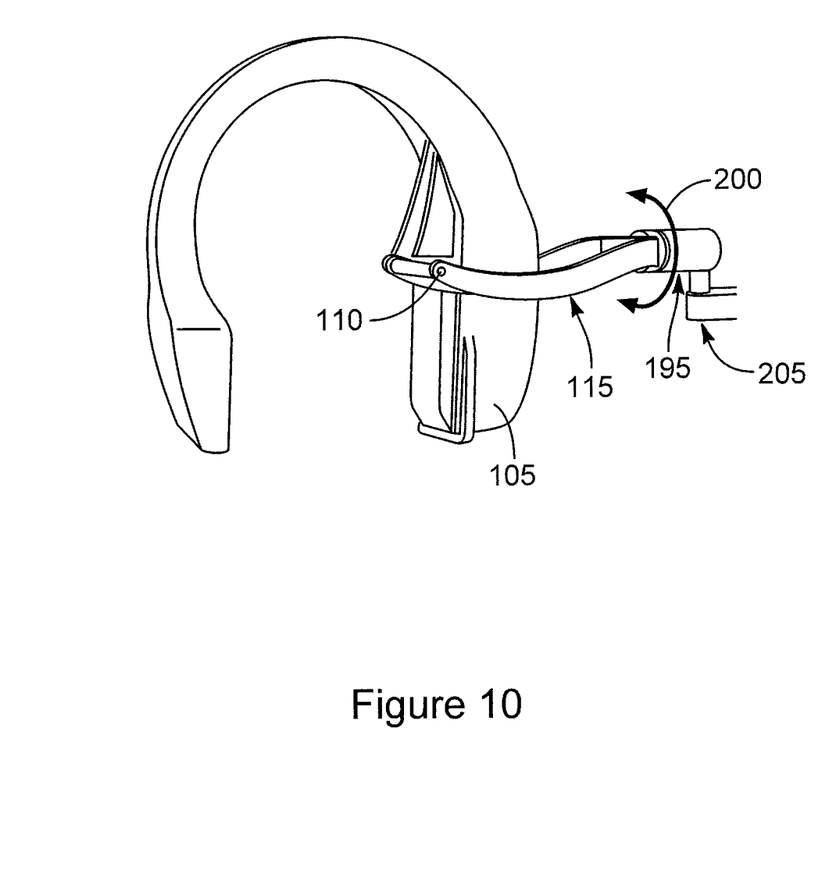
FIG. 10 shows a side perspective view of some embodiments of the imaging arm, which have been rotated laterally.

In some configurations, the imaging arm fork 115 optionally provides the imaging arm 105 with an axis of lateral rotation. FIG. 10 shows these configurations where the imaging arm fork 115 is attached to a lateral pivot joint 195, which allows the imaging arm fork to rotate clockwise and/or counter-clockwise, as indicated by the double pointed arrow 200. FIG. 10 shows some embodiments in which the imaging arm fork 115 has been rotated about 180 degrees from its standard position (shown in FIG. 1).

In some embodiments, the imaging fork arm 115 optionally provides the imaging arm 105 with an axis of horizontal rotation. FIG. 10 shows these embodiments in which the imaging arm fork 115 is attached to a horizontal pivot joint 205, which allows the imaging arm fork to pivot through a horizontal range of motion.

The imaging arm 105 can be connected (e.g., via the imaging arm fork 115) to any suitable support structure 120 that is capable of holding the imaging arm at a desired vertical and/or horizontal position. Indeed, in some configurations, the imaging arm is connected to a fixed support structure, such as a wall, a column, a floor, a shelf, a cabinet, a stationary frame, a ceiling, a door, a sliding structure, a bed, a gurney, a rail, and/or any other suitable support structure that is not intended to be easily moved and repositioned around a patient.

Figure 11:
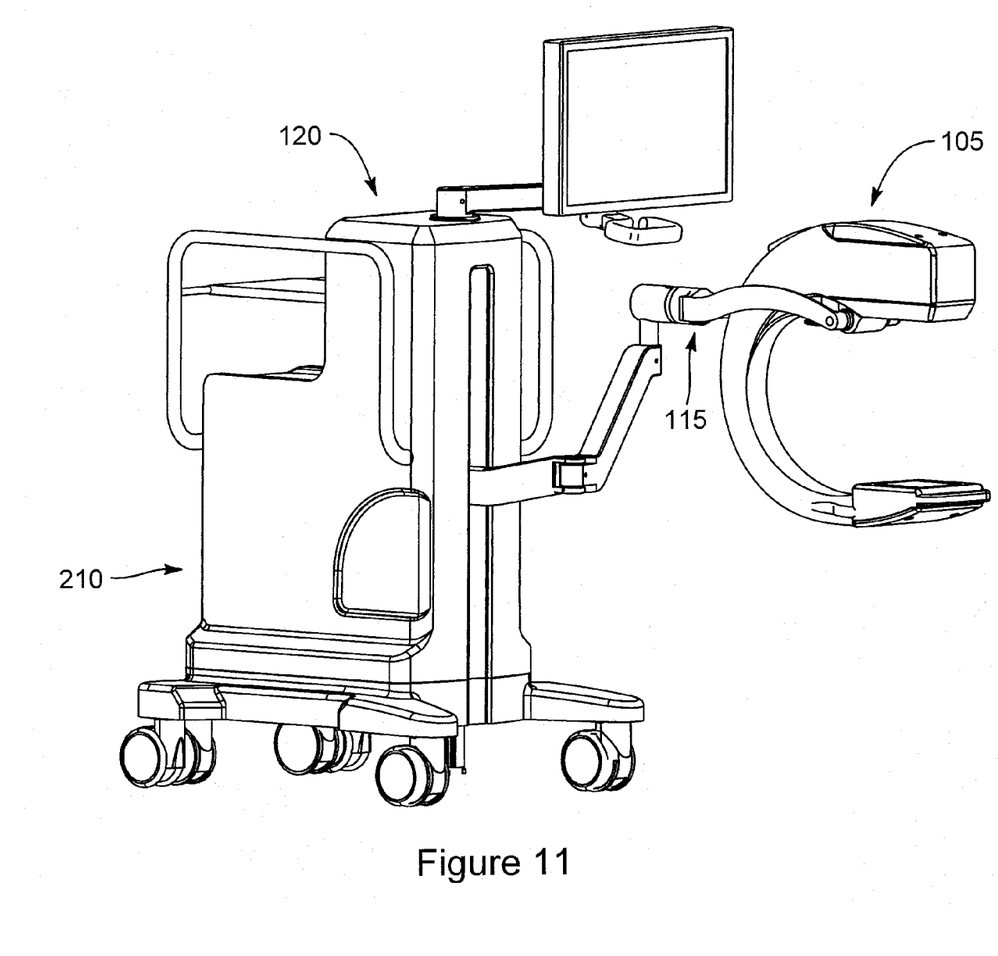
FIG. 11 shows a front-side perspective view of some embodiments the X-ray imaging arm attached to an X-ray imaging arm support structure.

In other configurations, though, the imaging arm 105 is connected to a movable support structure. In such configurations, the movable support structure can be configured to move across a floor while supporting the imaging arm. Thus, the movable support structure can comprise one or more wheels, shelves, handles, monitors, computers, stabilizing members, limbs, legs, struts, cables, and/or weights (to prevent the weight of the imaging arm and/or any other component from tipping the movable support structure). FIG. 11 shows some embodiments in which the movable support structure 120 comprises a wheeled structure 210 that supports the imaging arm 105.

Figure 12:
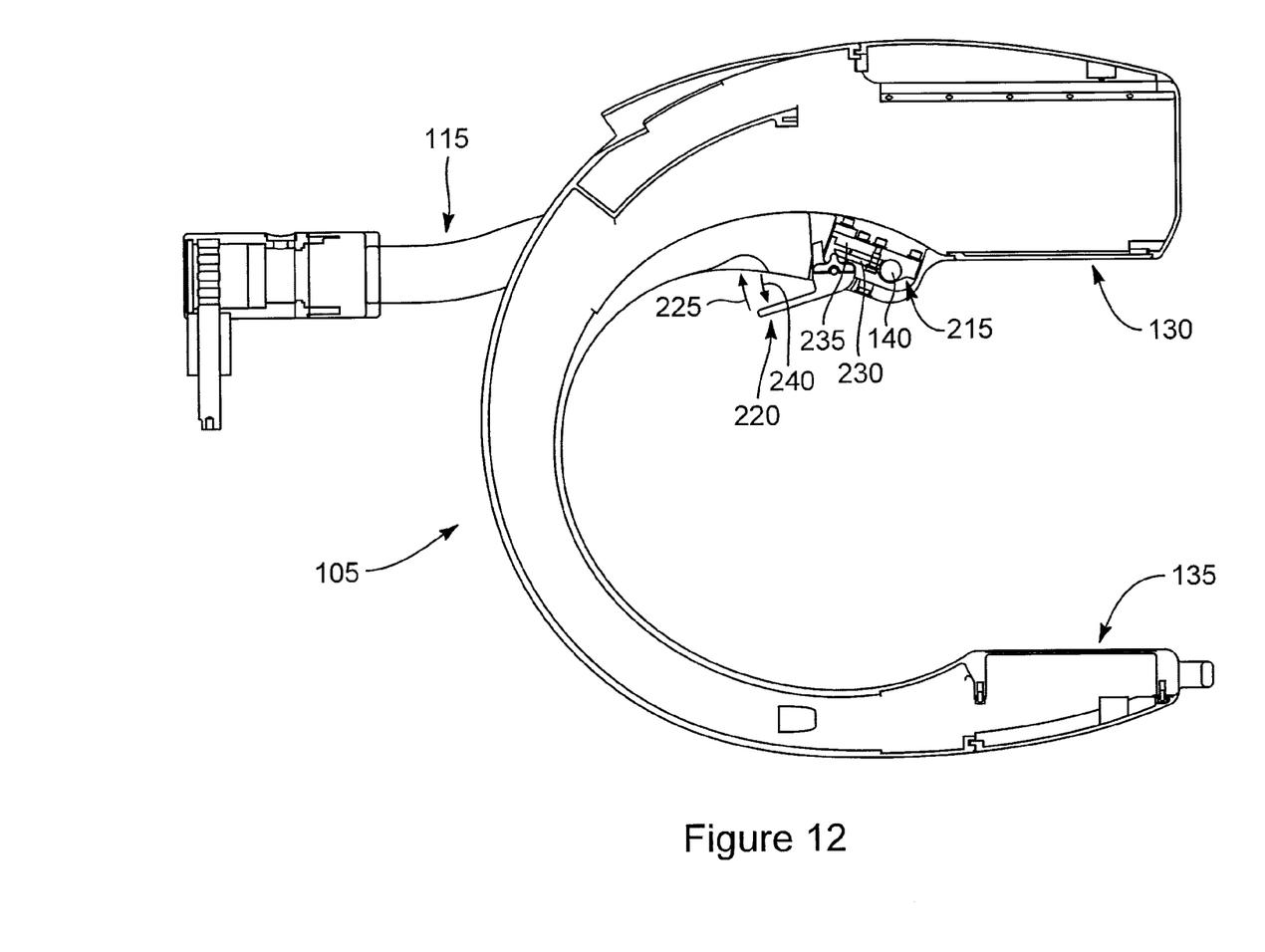
FIG. 12 shows a cross-sectional view of some embodiments of the imaging arm comprising a locking mechanism.

In some configurations, the pivoting X-ray device can comprise any suitable locking mechanism that can selectively lock and unlock the orbital rotation of the imaging arm 105. For instance, the locking mechanism can comprise a manually-engaged clamp, a detent mechanism, a motorized lock, an electric lock, a radio controlled lock, a remotely engaged clamp, and/or any other suitable mechanism that can be used to lock and release the orbital rotation of the imaging arm.

Where the locking mechanism comprises a manually-engaged clamp, it can selectively lock and unlock the orbital rotation of the imaging arm 105. FIG. 12 shows some embodiments in which the imaging arm 105 comprises a two-armed clamp 215 that wraps around a portion of the pivot pin 140. FIG. 12 also shows that the imaging arm 105 has a lever 220 that can be rotated (e.g., in the direction of arrow 225) to force the 2 arms 230 and 235 of the clamp 215 towards each other and, thereby, stop the rotation of the imaging arm 105 with respect to the pivot pin 140. In contrast, when the lever 220 is moved in the direction of arrow 240, the distance between the clamp's arms 230 and 235 is allowed to increase, causing the clamp to release the pivot pin and to allow the imaging arm to be rotated.

Figure 13:
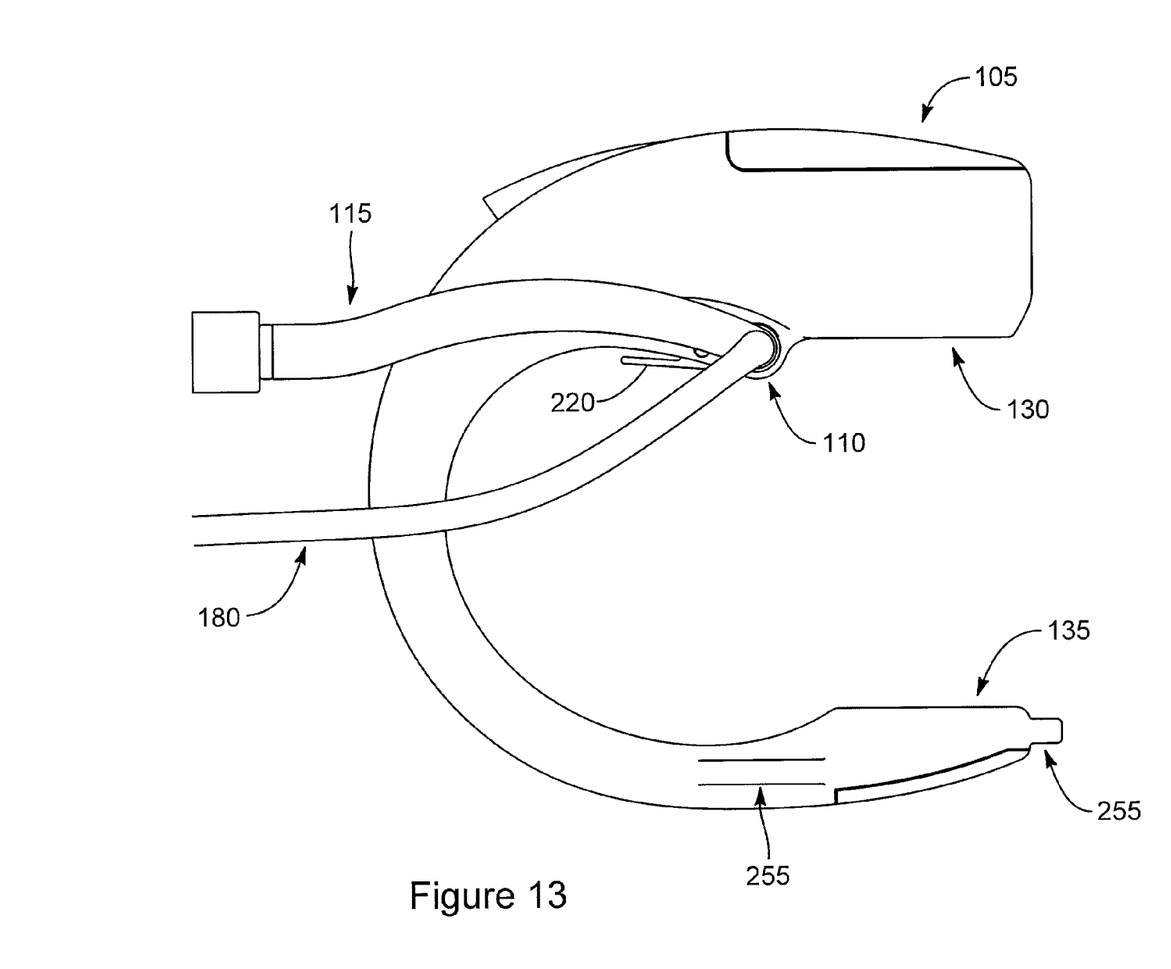
FIG. 13 shows a side plan view of some embodiments of the X-ray imaging arm, wherein a cable attaches to the imaging arm via an orbital pivot joint.

The pivoting X-ray device 100, the X-ray source 130, and/or the X-ray detector 135 can be configured to receive power and/or transfer data through one or more cables 180 that are connected to at least a portion of the imaging arm. Come conventional C-arms 15 that comprise a rail or raceway that prevents the power cable from entering the C-arm through an elongated portion 245 (see FIG. 1). In the pivoting X-ray device, though, the power cable can enter the imaging arm through any suitable position on the imaging arm. In some embodiments, FIG. 13 shows that the cable 180 is attached to a portion of the imaging arm 105 (e.g., the X-ray source and/or the X-ray detector 135) via the orbital pivot joint 110. In such embodiments, the cable can be connected to the various portions of the imaging arm in any suitable manner, including by being: threaded through the orbital pivot joint, anywhere on the imaging arm, anywhere on or in the fork, and/or connected to the imaging arm via a slip ring disposed at the orbital pivot joint.

The pivoting X-ray devices 100 described herein can be made in any suitable manner that forms the structures described. By way of example, the pivoting X-ray devices can be formed through a process involving molding, extruding, casting, cutting, stamping, bending, drilling, bonding, welding, mechanically connecting, frictionally connecting, and/or any other suitable process.

The described pivoting X-ray devices 100 can also be used for any x-ray imaging process. By way of example, an operator can orbitally rotate the imaging arm 105 by grabbing the arm (e.g., via a handle 255, shown in FIG. 13) and rotating the arm clockwise and/or counter-clockwise. Additionally, the operator can selectively lock the imaging arm at any suitable location in its orbital rotation and/or release the orbital rotation of the arm in any suitable manner (e.g., via lever 220).

The described pivoting X-ray devices 100 may have several useful features. First, unlike some conventional C-arms 15 that comprise semi-circular elongated portion 245 (see FIG. 1) that provides a side/rear capture point for an orbital rotation mechanism 255, the described imaging arm 105 does not roll or slide past a side or rear capture mechanism. As a result, the described imaging arm can have a smaller elongated portion, a different shaped elongated portion (e.g., an elongated portion that is squat, C-shaped; angled; V-shaped; convex-shaped, non-circular, etc.), be made from a lighter material (e.g., a polymer, plastic, composite material, carbon fiber and resin matrix, fabricated metal, etc.), be smaller overall, be easier to move and position, and/or be less expensive to produce than certain conventional C-arms 15. Second, the described imaging arm need not have a track, raceway, rail, or other mechanism that allows the imaging arm to rotate about a virtual pivot point; thus, less parts and simpler. Third, because the described imaging arm 105 can weigh less than some conventional C-arms 15, the described pivoting X-ray devices can weigh substantially less than some conventional C-arm positioning devices 10. Indeed, because the described imaging arm can weigh less than some conventional C-arms, the support structure used to support the described imaging arm may require less weight to prevent it from being tipped by the weight of the imaging arm than would a similar support structure that is used to support a conventional C-arm. Accordingly, the described pivoting X-ray devices may be easier to move (e.g., roll across a floor) than some conventional C-arm positioning devices. Fourth, because the imaging arm 105 can allow the cable 180 to enter the arm through the elongated portion 150 (e.g., because the arm need not rotate through a track), through the fork 115, and/or through the pivot joint 110, the imaging arm may help manage the cable placement and to keep the cable out of the way.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

The invention claimed is:

1. An X-ray imaging device, comprising:
   an X-ray source; and
   an X-ray detector, wherein the X-ray source and the X-ray detector are disposed at nearly opposing locations of an imaging arm; and
   a pivot joint that is physically attached to or part of the imaging arm which allows the imaging arm to have an axis of orbital rotation substantially coinciding with the center of gravity of the imaging arm.

2. The device of claim 1, wherein the pivot joint pivotally attaches the imaging arm to an X-ray imaging arm fork.

3. The device of claim 2, wherein the imaging arm fork comprises a first support arm that is pivotally attached to the pivot joint at a first side of the imaging arm.

4. The device of claim 2, wherein the imaging arm fork comprises two support arms that are pivotally attached to the imaging arm.

5. The device of claim 1, wherein an electrical cable electrically connects to a portion of the imaging arm via the pivot joint.

6. The device of claim 1, further comprising a locking mechanism that selectively locks and unlocks the imaging arm with respect to its axis of orbital rotation.

7. The device of claim 1, wherein the pivot joint allows the imaging arm to orbitally rotate more than about 180 degrees.

8. An X-ray system, comprising:
   an X-ray imaging device, comprising:
      an imaging arm;
      an X-ray source; and
      an X-ray detector, wherein the X-ray source and the X-ray detector are disposed at nearly opposing locations of the imaging arm; and
      a pivot joint that is directly attached to or part of the imaging arm which allows the imaging arm to have an axis of orbital rotation substantially coinciding with the center of gravity of the imaging arm;

an X-ray support fork that is pivotally attached to the imaging arm at the pivot joint; and a support structure configured to be moved across a floor.

9. The system of claim 8, wherein a center of gravity of the imaging arm substantially coincides with the pivot joint.

10. The system of claim 8, wherein the X-ray support fork comprises a first support arm that is pivotally attached to the pivot joint at a first side of the imaging arm.

11. The system of claim 8, wherein the X-ray support fork comprises two support arms that are pivotally attached to the imaging arm.

12. The system of claim 8, further comprising a locking mechanism that selectively locks and unlocks the imaging arm with respect to its axis of orbital rotation.

13. The system of claim 8, wherein the pivot joint allows the imaging arm to orbitally rotate more than about 180 degrees.

14. The system of claim 8, wherein the detector comprises a housing.

15. An X-ray system, comprising:
an X-ray imaging device comprising:
an imaging arm;
an X-ray source; and
an X-ray detector, wherein the X-ray source and the X-ray detector are disposed at nearly opposing locations of the imaging arm; and
a pivot joint that is directly attached to the imaging arm which allows the imaging arm to have an axis of orbital rotation substantially coinciding with the center of gravity of the imaging arm; and an X-ray imaging arm fork having a first end pivotally attached to the pivot joint to support the imaging arm; and an X-ray imaging arm support structure that is connected to a second end of the fork, the support structure configured to be moved across a floor.

16. The system of claim 15, wherein a center of gravity of the imaging arm substantially coincides with the pivot joint.

17. The system of claim 15, wherein the pivot joint comprises a stop mechanism that limits a range of orbital rotation of the imaging arm.

18. The system of claim 15, further comprising a locking mechanism that selectively locks and unlocks the imaging arm with respect to its axis of orbital rotation.

19. The system of claim 15, wherein an electrical cable electrically connects to a portion of the imaging arm via the pivot joint.

20. The system of claim 15, wherein the fork comprises a lateral pivot joint that provides a lateral axis of rotation for the imaging arm.

21. The system of claim 15, wherein the pivot joint allows the imaging arm to orbitally rotate more than about 180 degrees.

* * * * *